US012766261B2

(12) United States Patent
Murier et al.

(10) Patent No.: US 12,766,261 B2
(45) Date of Patent: Oct. 20, 2026

(54) AUTOINJECTOR FOR AUTOMATIC INJECTION OF A MEDICAL PRODUCT INTO AN INJECTION SITE

(71) Applicant: Becton Dickinson France, Le Pont-de-Claix (FR)

(72) Inventors: Arnaud Murier, Grenoble (FR); Vincent Delobelle, Domene (FR); Michael Fiard, Eybens (FR)

(73) Assignee: Becton Dickinson France, Le Pont-de-Claix (FR)

( * ) Notice: Subject to any disclaimer, the term of this patent is extended or adjusted under 35 U.S.C. 154(b) by 628 days.

(21) Appl. No.: 18/215,865

(22) Filed: Jun. 29, 2023

(65) Prior Publication Data

US 2024/0001033 A1 Jan. 4, 2024

(30) Foreign Application Priority Data

Jul. 1, 2022 (EP) .................................... 22305984

(51) Int. Cl.
*A61M 5/20* (2006.01)
*A61M 5/315* (2006.01)

(52) U.S. Cl.
CPC .......... *A61M 5/20* (2013.01); *A61M 5/31501* (2013.01)

(58) Field of Classification Search
CPC ........... A61M 2005/31508; A61M 2005/3151; A61M 5/31513
See application file for complete search history.

(56) References Cited

U.S. PATENT DOCUMENTS

| | | | | |
|---|---|---|---|---|
| 1,687,091 A * | 10/1928 | Hein | A61M 5/31513 | 604/222 |
| 10,675,412 B2 * | 6/2020 | Jones | F04B 13/00 | |
| 2012/0253292 A1 * | 10/2012 | Ivosevic | A61M 5/31515 | 604/222 |
| 2012/0283662 A1 * | 11/2012 | MacDonald | A61M 5/31511 | 604/236 |
| 2017/0290981 A1 * | 10/2017 | Hoeholt | A61M 5/315 | |
| 2023/0010593 A1 * | 1/2023 | Cammish | A61F 9/0017 | |

FOREIGN PATENT DOCUMENTS

| | | |
|---|---|---|
| JP | 2009028527 A | 2/2009 |
| WO | 2020152034 A1 | 7/2020 |
| WO | 2020190529 A1 | 9/2020 |
| WO | 2021115819 A1 | 6/2021 |

* cited by examiner

*Primary Examiner* — William R Carpenter
(74) *Attorney, Agent, or Firm* — The Webb Law Firm

(57) ABSTRACT

The autoinjector includes a housing extending along longitudinal axis (A) and configured to receive a medical container having a barrel defining a reservoir for containing a medical product, said barrel having a distal end provided with an injection needle and an opened proximal end. A power pack arranged inside the housing for expelling the medical product from the medical container. The power pack includes a plunger rod configured to extend through the opened proximal end of the barrel for pushing a stopper arranged inside the barrel. The plunger rod is axially movable between an initial position and an injection end position distally located with respect to the initial position. Resilient adjustment means are arranged between the plunger rod and the barrel for compensating clearances between the plunger rod and the barrel.

13 Claims, 4 Drawing Sheets

AUTOINJECTOR FOR AUTOMATIC INJECTION OF A MEDICAL PRODUCT INTO AN INJECTION SITE

CROSS-REFERENCE TO RELATED APPLICATION

This application claims priority to European Patent Application No. 22305984.1 filed Jul. 1, 2022, the disclosure of which is hereby incorporated by reference in its entirety.

BACKGROUND OF THE INVENTION

Field of the Invention

The present invention relates to an autoinjector.

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction away from the user's hand, and the "proximal direction" is to be understood as meaning the direction toward the user's hand.

Description of Related Art

Automatic injection devices are designed for automatic injection of a medical product into an injection site. Autoinjectors usually comprise a top body and a bottom body assembled to each other to form a housing. The bottom body is usually configured for receiving a medical container, such as a prefillable or prefilled syringe. The medical container has a barrel defining a reservoir for containing the medical product, the barrel having a distal end provided with an injection needle and an opened proximal end receiving a plunger rod for pushing a stopper. The injection needle is usually protected by a rigid needle shield removably secured to a distal tip of the medical container.

Autoinjectors also include a safety shield mechanism moving from an extended to a retracted position to respectively shield or unveil the needle and a power pack for automatically injecting the medical product into an injection site. The power pack is usually arranged inside the top body and includes a plunger rod for pushing a stopper inside the barrel of the medical container. An initially compressed spring is configured for moving the plunger in the distal direction. Locking means are provided for maintaining the plunger rod in an initial position in which the plunger rod is axially blocked despite the action of the compressed spring. A release member is further provided to release the plunger rod from the locking means and allow the spring to push the plunger rod in the distal direction to perform injection. A predetermined displacement of the safety shield towards the retracted position is required to allow the release member to unlock the locking means and release the plunger rod.

Assembly of the top body and the bottom body may be realized by any appropriate means such as snap-fitting or friction fit means. When fully assembled, a rattling noise may however be heard if a user shakes the autoinjector. This rattling noise is due to axial gaps that may exist between the powerpack and the medical container and between the power pack and the top body in the radial direction. As can be seen in FIGS. 1A-1B, the powerpack 6' may slightly move between a position (FIG. 1A) in which the powerpack abuts against the top body 2B' (and an axial clearance exists between the powerpack and the medical container 100') and another position (FIG. 1B) in which the powerpack 6' abuts against the medical container 100' (and an axial clearance exists between the powerpack and the top body).

The document WO2021115819 discloses an injection device for expelling a dose of a medicament. The document WO2020190529 discloses an automatic injection system. The document WO2020152034 discloses a delivery system comprising a cartridge storing a liquid, and a dosing mechanism to dispense a predetermined amount of liquid from the cartridge. The document JP2009028527 discloses a syringe.

There is therefore a need for reducing these clearances and limiting the rattling noise.

SUMMARY OF THE INVENTION

An aspect of the invention is an autoinjector for automatic injection of a medical product into an injection site, the autoinjector including:

- a housing extending along longitudinal axis A and configured to receive a medical container having a barrel defining a reservoir for containing a medical product, said barrel having a distal end provided with an injection needle and an opened proximal end,
- a power pack arranged inside the housing for expelling the medical product from the medical container, the power pack including a plunger rod configured to extend through the opened proximal end of the barrel for pushing a stopper arranged inside the barrel, the plunger rod being axially movable between an initial position and an injection end position distally located with respect to the initial position,
- resilient adjustment means arranged between the plunger rod and the barrel for compensating clearances between the plunger rod and the barrel.

The autoinjector of the invention thus removes the axial and radial clearances between the power pack and the medical container. As a result, the rattling noise is removed.

The autoinjector may further include some or all of the features below.

In an embodiment, the resilient adjustment means include a spring blade configured to deform in a radial inward direction so that the spring blade exerts a radial pushing force against the inner lateral wall of the barrel.

In an embodiment, the spring blade has a fixed end secured to the plunger rod and a friction element configured to frictionally engage the inner lateral surface of the barrel.

In an embodiment, the friction element is distally located with regard to the fixed end.

In an embodiment, the friction element is arranged at a free end of the spring blade.

In an embodiment, the spring blade includes an inclined outer side arranged between the fixed end and the friction element for easing insertion of the plunger inside the opened proximal end of the barrel.

In an embodiment, the outer side has a convex and curved shape.

In an embodiment, the resilient adjustment means are located at the distal end of the plunger rod.

In an embodiment, the resilient adjustment means include a distal pushing area configured to push against the stopper.

In an embodiment, the resilient adjustment means and the plunger rod form a single piece.

In an embodiment, the resilient adjustment means are overmolded on the plunger rod.

In an embodiment, the resilient adjustment means are arranged on a plug attached to a distal end of the plunger rod.

In an embodiment, the plug includes a distal abutment surface configured to distally push against the stopper when the plunger rod moves to the injection end position.

In an embodiment, the plug includes a proximal shoulder configured to abut against a distal abutment surface of the plunger rod to stop insertion of the plug inside the plunger rod.

BRIEF DESCRIPTION OF THE DRAWINGS

The invention and the advantages arising therefrom will clearly emerge from the detailed description that is given below with reference to the appended drawings as follows.

DESCRIPTION OF THE INVENTION

Figure 1A:
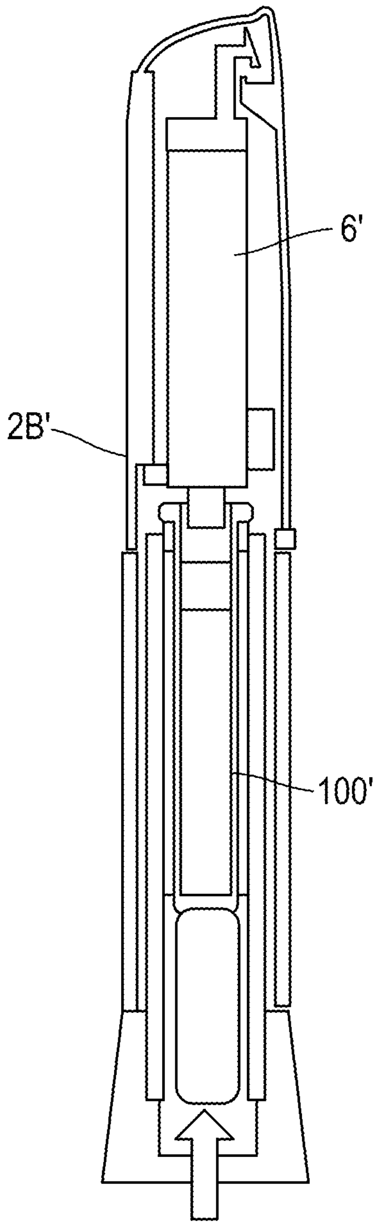
FIGS. 1A and 1B are schematic views illustrating the clearances of an autoinjector which is not part of the invention in, respectively, a first position in which the power pack abuts against the top body and a second position in which the power pack abuts against the syringe flange.
Figure 1B:
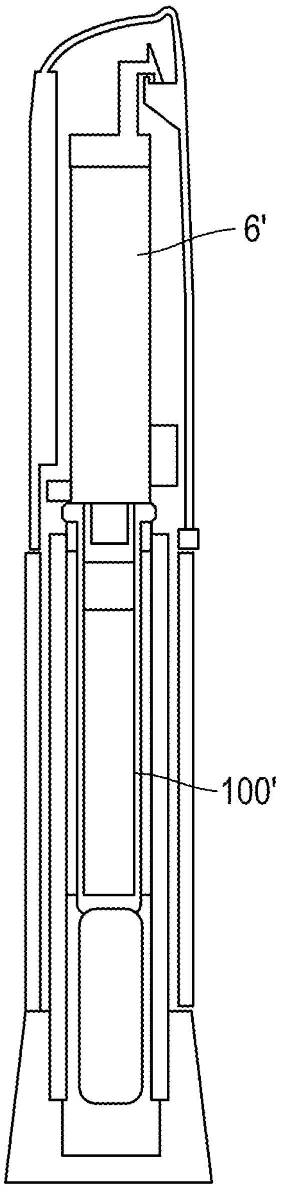
Figure 2:
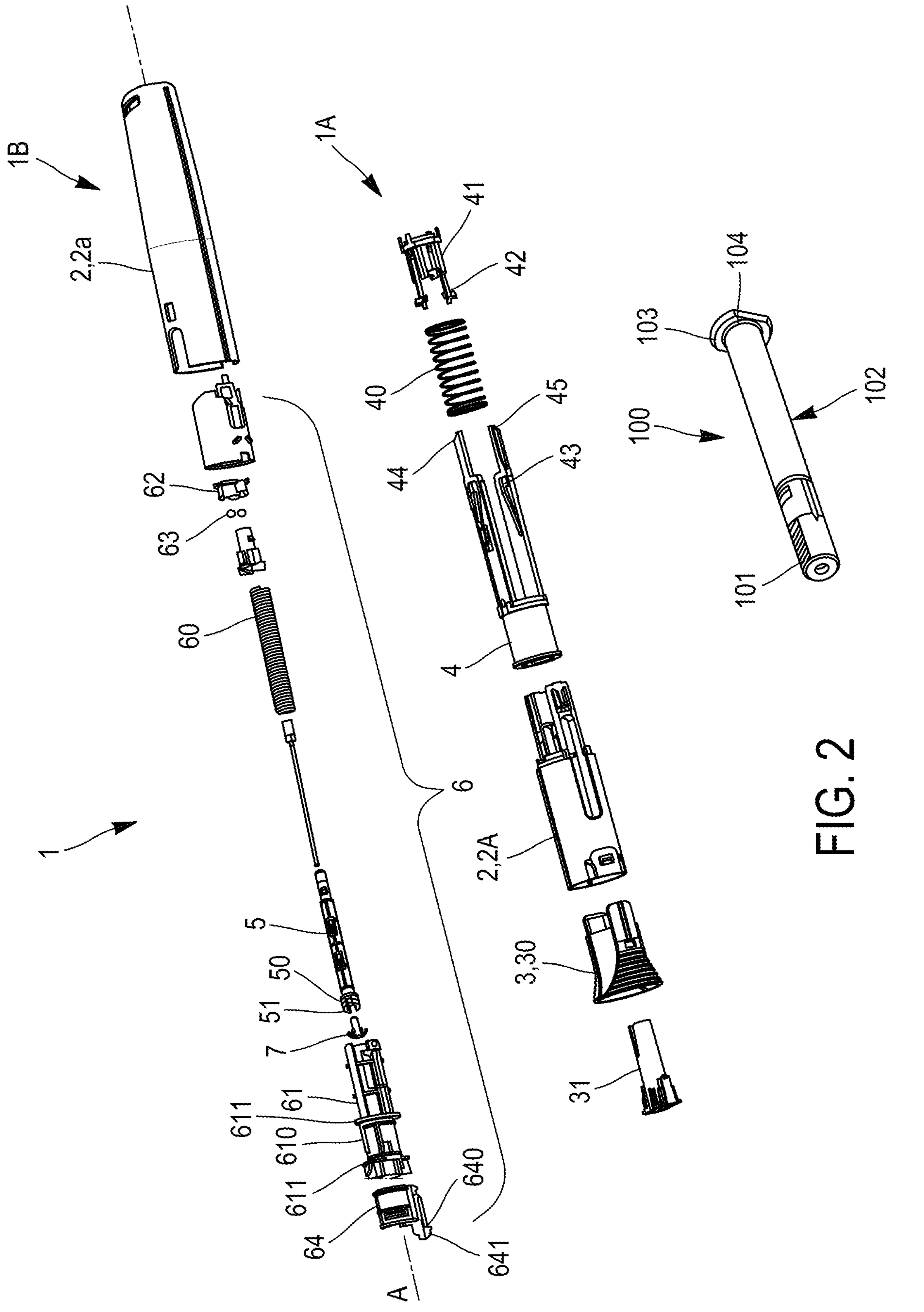
FIG. 2 is an exploded view of an autoinjector according to an embodiment of the invention.

With reference to FIG. 2 is shown an autoinjector 1 according to an embodiment of the invention. The autoinjector 1 is designed for automatic injection of a product into an injection site. The autoinjector 1 extends along a longitudinal axis A. The autoinjector 1 has a housing 2 which may be formed by a bottom body 2A of a lower sub-assembly 1A and a top body 2B of a top sub-assembly 1B. The bottom body 2A and the top body 2B of the housing 2 may be assembled to each other by any appropriate securing means such as, for instance, snap-fitting means.

The lower sub-assembly 1A includes a bottom body 2A for receiving a medical container 100, a cap 3 including an outer housing 30 removably attached to a distal end of the bottom body 2A and a retainer 31 configured for removing a needle shield 101 when the outer housing 2 is removed from the bottom body 2A, and a needle cover 4 axially movable along the longitudinal axis A with respect to the bottom body 2A between a first extended position (pre-use position) in which the needle cover 4 at least partially or completely shields an injection needle, a retracted position (injection position) proximally located relative to said first extended position, in which the needle cover 4 moves inside the autoinjector 1 to trigger the injection, and a second extended position (safety position) in which the needle cover 4 moves back in the distal direction so as to safely shield the injection needle. Movement of the needle cover 4 in the proximal direction from the first extended position to the retracted position is caused by a distal end of the needle cover 4 being pressed against an injection site during use of the autoinjector 1. The lower sub-assembly 1A may further include a safety spring 40 for urging the needle cover 4 in the distal direction towards the safety position. Locking means may be provided for locking the needle cover 4 in said safety position. The locking means may include a locking element, such as an abutment ring 41 configured to be fixed to the medical container 100, having a proximally extending resilient leg 42 that engages a two-way slot 43 arranged through the needle cover 4.

As visible in FIG. 2, the medical container 100 has a tubular barrel 102 defining a reservoir for containing a medical product to be injected. The barrel 102 has a distal end including a distal shoulder and a longitudinally protruding tip provided with an injection needle. A needle shield 101 is removably attached to said distal end for protecting and sealing the injection needle. Opposite its distal end, the barrel 102 has an opened proximal end 103 surrounded by a flange 104. The opened proximal end 103 is configured to receive a plunger rod 5 for pushing a stopper 105 (FIGS. 3A, 4C) arranged inside the barrel 102. The medical container 100 may be a prefilled or prefillable syringe.

Still with reference to FIG. 2, the top sub-assembly 1B includes a top body 2B arranged for receiving a power pack 6 configured to automatically expel the medical product contained within the medical container. The power pack 6 is the unit that stores the energy and contain the features necessary to hold and release said energy so as to expel the medical product from the medical container. The power pack 6 may include a plunger rod 5 for pushing the stopper 105 inside the barrel 102, biaising means such as an injection spring 60 for moving the plunger rod 5 in the distal direction, locking means for axially blocking the plunger rod 5 in an initial position before activation of the autoinjector 1, and a holder 61 for releasing said locking means and thus allowing distal movement of the plunger rod 5 when the autoinjector 1 is activated.

The plunger rod 5 is axially movable with respect to the housing 2 between an initial position, in which the plunger rod 5 is axially blocked by the locking means against the action of the injection spring and an injection end position, distally located with regard to the initial position, in which the injection is completed and in which the plunger rod 5 may press the stopper 105 against a distal end of the reservoir formed by the barrel 102. In the initial position (see FIG. 3A or 4C), the plunger rod 5 may extend through the opened proximal end 103 inside the barrel 102 and a distal end 50 of the plunger rod 5 may, or may not, be axially away from the stopper 105. The distal end 50 of the plunger rod 5 defines a distal pushing surface 51 which may be orthogonal to the longitudinal axis A and which is configured to abut against a proximal end 106 of the stopper 105 to push the stopper 105 in the distal direction. The distal pushing surface 51 may be in the form of an annular or C-shaped ring.

The locking means may include a blocking ring 62 axially movable between a locking position, in which the blocking ring 62 may maintain blocking balls 63 engaged inside radial cavities of the plunger rod 5, and a release position, proximally located with regard to the locking position, in which the blocking ring 62 allows the blocking balls 63 to move outside the radial cavities of the plunger rod 5 such that the plunger rod 5 is no longer blocked by said locking balls and may move in the distal direction under the action of the injection spring 60 to perform the injection operation. Movement of the blocking ring 62 from the locking position to the release position may be caused by a proximal end of the holder 61 pushing said blocking ring 62 while moving to the triggering position.

The holder 61 is axially movable inside the top body 2B between an initial position before activation of the autoinjector 1 and a triggering position, proximally located with regard to the initial position, in which the holder 61 releases the plunger rod 5 from the locking means so that the plunger rod 5 can move distally under the action of the injection spring 60. In the initial position, the holder 61 may be axially away from the blocking ring 62 while in the triggering position a proximal end of the holder 61 may abut against the blocking ring 62 and may have pushed the blocking ring 62 in the release position. The holder 61 is therefore configured to trigger the injection operation. Proximal movement of the holder 61 from the initial position to the triggering position is caused by a proximal end of a proximally extending leg 44 of the needle cover 4 abutting against a distal end of the holder 61 when the needle cover 4 is moved to the retracted position.

Still with reference to FIG. 2, the holder 61 may include a circular groove 610 for receiving a rotatable locker 64 configured for preventing inadvertent movement of the holder 61 to the triggering position. The circular groove 610 may extend between two radial flanges 611 arranged for axially blocking the locker 64 such that the locker 64 moves together with the holder 61 in the axial direction.

The locker 64 may be in the form of a C-shaped ring and is axially movable with respect to the top body 2B between a an initial position, in which a proximal surface 640 of the locker 64 is axially away from a distal surface of an axial rib of the top body 2B, and an intermediate blocking position, proximally located with regard to said initial position, in which the proximal surface 640 of the locker 64 abuts the distal surface of the axial rib of the top body 2B such that the locker 64 blocks the holder 61 which cannot transition to the triggering position. The locker 64 accordingly prevents inadvertent activation of the autoinjector 1. Proximal movement of the locker 64 from the initial position to the intermediate blocking position is caused by a proximal end of a proximally extending leg 45 of the needle cover 4 abutting against a cam surface 641 of the locker 64 when the needle cover 4 is moved towards the retracted position.

The locker 64 is further rotatable with respect to the holder 61 between the above described intermediate blocking position and a release position, in which the proximal surface 640 of the locker 64 is circumferentially shifted away the distal surface of the top body 2B. In the release position, the locker 64 is thus no longer prevented by the top body 2B to move in the proximal direction. Therefore, the holder 61 can move to the triggering position. Rotation of the locker 64 from the intermediate blocking position to the release position is caused by the proximally extending leg 45 of the needle cover 4 sliding against the cam surface 640 of the locker 64 when the needle cover 4 is moved towards the retracted position The autoinjector 1 further includes resilient adjustment means arranged between the plunger rod 5 and the medical container 100 for compensating the radial and axial clearances between the powerpack 6, the top body 2B and the medical container 100. Thus, the resilient adjustment means are configured to remove the rattling noise.

Figure 3A:
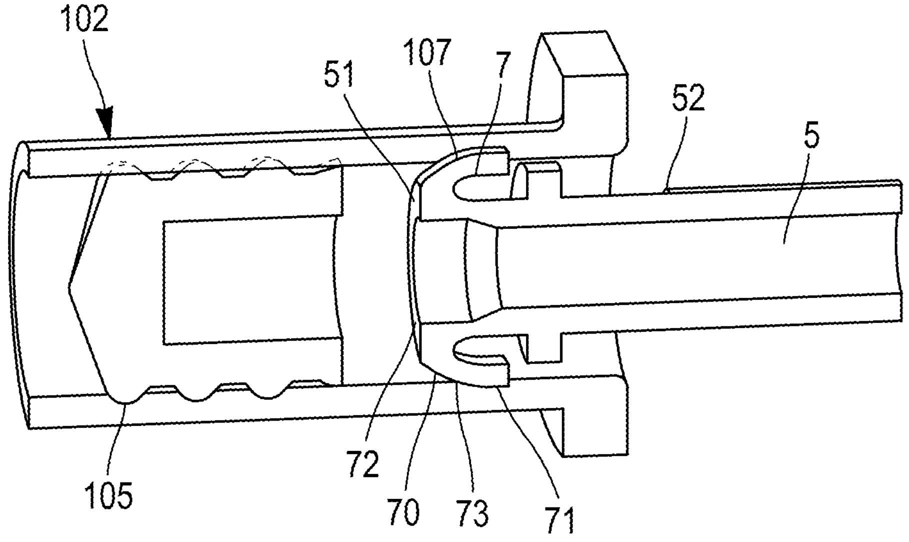
FIGS. 3A, 3B and 3C are cross-section views illustrating a barrel and a plunger rod of an autoinjector according to an embodiment of the invention.
Figure 3B:
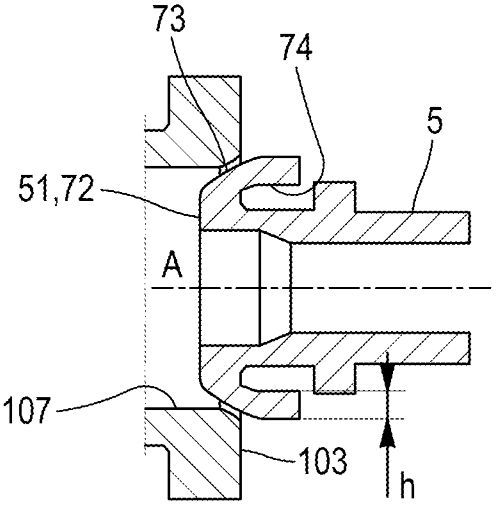
Figure 3C:
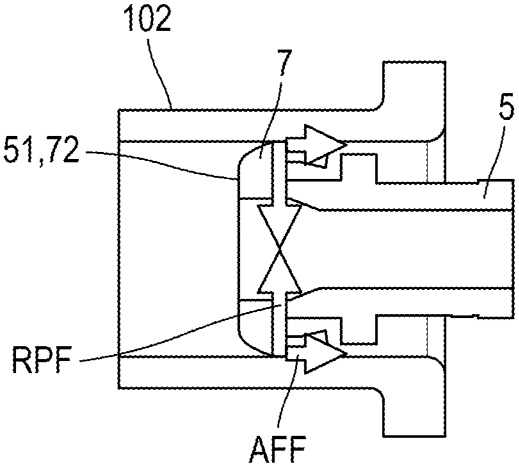

With reference to FIGS. 3A to 3C, the resilient adjustment means include one or several spring blades 7 arranged between an outer lateral surface 52 of the plunger rod 5 and an inner lateral surface 107 of the barrel 102. The resilient adjustment means may include two diametrically opposite spring blades 7, although this number may vary, the adjustment means including for example three or more spring blades 7 regularly distributed in a circumferential direction.

In the embodiment illustrated in FIGS. 3A to 3C, the spring blades 7 and the plunger rod 5 form a single piece. For instance, the spring blades 7 and the plunger rod 5 are made of a single piece of the same material. Alternatively, the spring blades 7 and the plunger rod 5 may be made of two different materials, the spring blades 7 being overmolded on the plunger rod 5. For instance, the spring blades 7 may be made of a thermoplastic elastomer (TPE).

The spring blades 7 include a fixed end 70 secured to the plunger rod 5 and a free end configured to abut and rub against the barrel 102. The fixed end 70 is distally located with regard to the free end.

The spring blades 7 are resiliently deformable in a radial direction. That is, their free end moves in a radially inward direction when the spring blade 7 deforms against the inner lateral surface 107 of the barrel 102. As a result, the spring blades 7 exert a pushing force against the barrel 102 which, in turn, exerts a radial pushing force RPF on the plunger rod 5 (FIG. 3C). Since the plunger rod 5 is part of the power pack 6, the spring blades 7 thus compensate the radial clearance between the powerpack 6 and the top body 2B. The power pack 6 is thus prevented from clinking against the top body 2B.

The spring blades 7 include a friction element 71, which may be arranged at their free end, configured to frictionally engage and rub against the inner lateral surface 107 of the barrel 102, thereby generating an axial friction force AFF (FIG. 3C). The friction element 71 thus opposes axial movements of the power pack 6 pack relative to the barrel 102. As a result, the axial clearance is removed and the power pack 6 cannot clink against the medical container 100. The rattling noise is removed. The friction element 71 may be a contact area, or a contact edge which may be orthogonal to the longitudinal axis A, provided at an outer side 73 of the spring blade. The friction element 71 and the inner lateral surface 107 of the barrel 102 may be complementarily shaped.

The spring blade 7 extends at the distal end 50 of the plunger rod 5. This allows the spring blade 7 to help distribute the axial effort against the proximal end 106 of the stopper 105 when the plunger moves in the distal direction during an injection operation. The spring blade 7 may accordingly define a distal pushing area 72, which may be arranged at the fixed end 70, for abutting against a proximal end 106 of the stopper 105. The distal pushing area 72 of the spring blade 7 may be orthogonal to the longitudinal axis A and may lengthen the distal pushing surface 51 of the plunger rod 5. Thus, as illustrated in FIG. 3A, the fixed end 70 and possibly the outer side 73 of the spring blade 7 may form an extension of the distal pushing surface 51 of the plunger rod 5.

Although the radial spring blades 7 oppose slight axial movements of the plunger rod 5 (and thus the power pack 6) towards the medical container 100 to avoid a rattling noise, the radial spring blades 7 must also allow the plunger rod 5 to move from the initial position to the injection end position. That is, the axial friction force AFF has to stay low in comparison with the force exerted by the injection spring 60 on said plunger rod 5. To that end, the radial spring blades 7 may have a straight or curved shape, a convex outer side 73, a concave inner side 74, a polygonal (such as a square or rectangular) cross section, an increasing height h or width w towards their free end, or any combination thereof. A curved outer side 73 of the spring blades 7 also eases insertion of the plunger rod 5 through the opened proximal end 103 of the barrel 102, as illustrated in FIG. 3B.

Figure 4A:
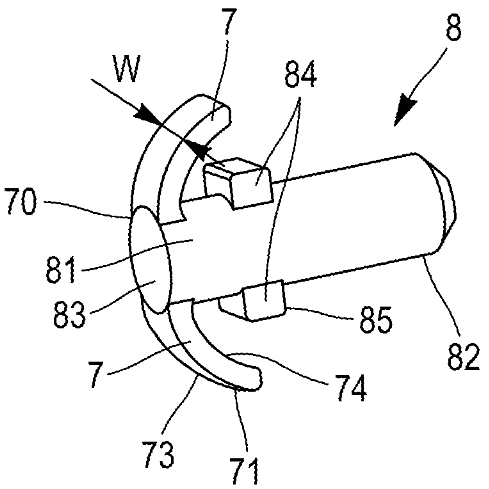
FIG. 4A is a perspective view of a plug of an autoinjector according to an embodiment of the invention.
Figure 4B:
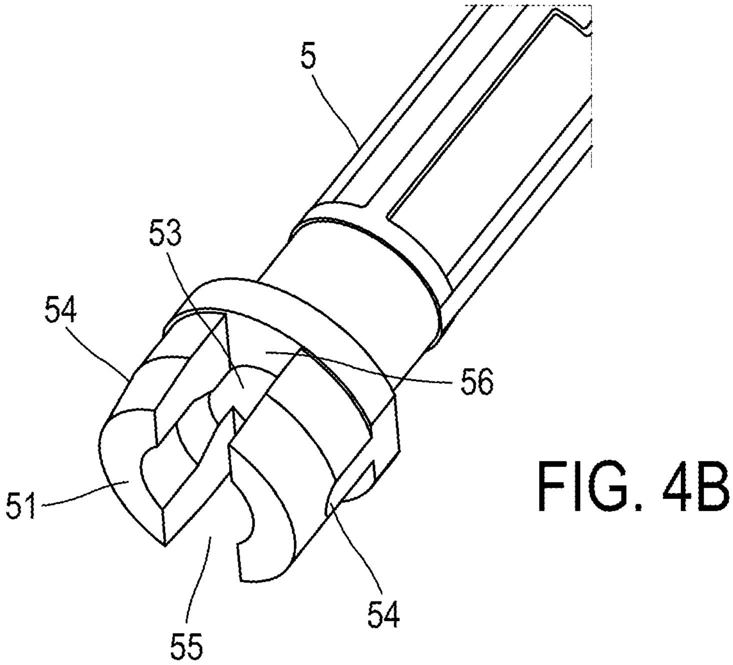
FIG. 4B is a perspective view of a plunger rod of an autoinjector according to an embodiment of the invention.
Figure 4C:
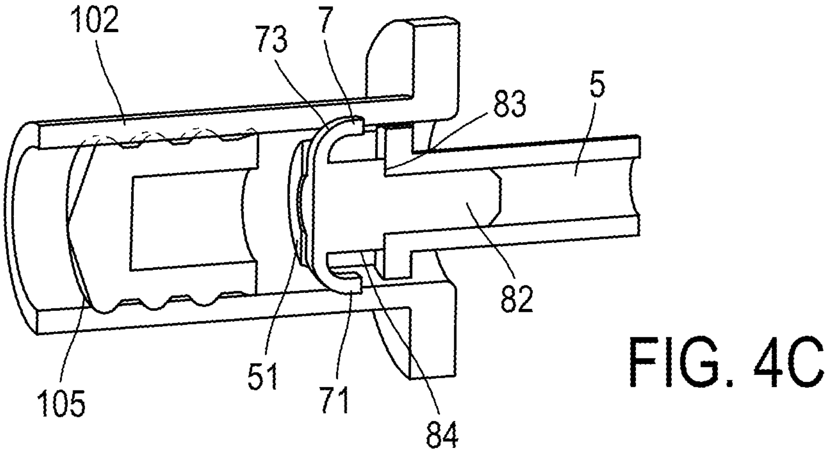
FIG. 4C is a cross-section view of a barrel and a plunger rod of an autoinjector according to an embodiment of the invention.

The spring blades 7 illustrated in FIGS. 4A and 4C are similar to the spring blades 7 of FIGS. 31-3C, except that they are provided on a part which is distinct from the plunger rod 5 and which is initially separate from the plunger rod 5. More specifically, the spring blades 7 are located on an outer lateral surface 80 of a plug 8 which is configured to be assembled to the plunger rod 5.

The plug 8 may be in the form of a cylindrical stem and includes a distal portion 81 provided with the spring blades 7 and a proximal connecting portion 82 for securing the plug 8 to the plunger rod 5 by any appropriate means such as friction-force, gluing or snap-fitting means. The distal portion 81 of the plug 8 may define a distal abutment surface 83 which may be orthogonal to the longitudinal axis A and which may be configured for abutting against a proximal end 106 of the stopper 105. As a result, the distal end of the plug 8 may be an extension of the distal pushing surface 51 of the plunger rod 5.

As illustrated in FIG. 4B, the plunger rod 5 may include a distal opening 53 for receiving the connecting portion 82 of the plug 8. The distal opening 53 and the connecting portion 82 may be complementarily shaped. The plunger rod 5 also includes one or several distally protruding circumferential walls 54 whose distal end defines the distal pushing surface 51 of the plunger rod 5. The distal pushing surface 51 of the plunger rod 5 may thus have a circular arc shape. The plunger rod 5 further includes axial slots 55 arranged for separating the circumferential walls 54 and configured to receive the spring blades 7. The axial slots 55 may be wider than the spring blades 7 so that the spring blades 7 may deform without being hampered by the circumferential walls 54. The axial slots 55 have an opened distal end for allowing insertion of the spring blades 7 therein, and an opposite proximal end which may define a distal abutment surface 56 for stopping insertion of the plug 8 inside the plunger rod 5. The distal abutment surface 56 may be proximally located with regard to the distal pushing surface 51 of the plunger rod 5.

The plug 8 may include one or several proximal shoulders 85 which may be arranged at a proximal end of radial protrusions 84 for abutting against the distal abutment surface 56 of the plunger rod 5. The connecting portion 82 of the plug 8 is preferably longer than the distal portion 81, said distal portion 81 extending from the distal end of the plug 8 to the proximal shoulders 85 while the connecting portion 82 extends from the proximal shoulders 85 to a proximal end of the plug 8. It is also contemplated that the radial protrusions 84 of the plug 8 are arranged at an axial distance from the fixed end 70 of the spring blades 7 and at a radial distance from their free end so that the radial protrusions 84 do not hinder the deformation of the resilient spring blades 7.

The spring blades 7 are resiliently deformable in a radial direction. That is, their free end moves in a radially inward direction when the spring blade 7 deforms against the inner lateral surface 107 of the barrel 102. As a result, the spring blades 7 exert a pushing force against the barrel 102 which, in turn, exerts a radial pushing force RPF on the plunger rod 5 (like in FIG. 3C).

The spring blades 7 include a friction element 71, which may be arranged at their free end, configured to frictionally engage and rub against the inner lateral surface 107 of the barrel 102, thereby generating an axial friction force AFF (like in FIG. 3C). The friction element 71 may be a contact area, or a contact edge which may be orthogonal to the longitudinal axis A, provided at an outer side 73 of the spring blade. The friction element 71 and the inner lateral surface 107 of the barrel 102 may be complementarily shaped.

As visible in FIGS. 4A and 4C, the fixed end 70 of the spring blades 7 is indirectly secured to the plunger rod 5, i.e. via the plug 8. The spring blades 7 and the plug 8 may be made of a single piece. The spring blades 7 may also be overmolded on the plug 8. For instance, the spring blades 7 are made of a thermoplastic elastomer (TPE).

The spring blade 7 extends at the distal end of the plug 8 (and thus at the distal end 50 of the plunger rod 5), i.e. at the distal-most portion of the plug 8. The spring blades 7 may accordingly define a distal pushing area 72, which may be arranged at their fixed end 70, for abutting against the proximal end 106 of the stopper 105. The distal pushing area 72 of the spring blades 7 may be orthogonal to the longitudinal axis A and may form an extension of the distal abutment surface of the plug 8 and/or of the distal pushing surface of the plunger rod 5.

In order to have the axial friction force AFF stay low in comparison with the force exerted by the injection spring 60 on said plunger rod 5, the radial spring blades 7 may have a straight or curved shape, a convex outer side 73, a concave inner side 74, a polygonal (such as a square or rectangular) cross section, an increasing height h or width w towards their free end, or any combination thereof. A curved outer side 73 of the spring blades 7 also eases insertion of the plunger rod 5 through the opened proximal end 103 of the barrel 102.

The invention claimed is:

1. An autoinjector for automatic injection of a medical product into an injection site, the autoinjector comprising:
- a housing extending along a longitudinal axis (A) and configured to receive a medical container having a barrel defining a reservoir for containing a medical product, said barrel having a distal end provided with an injection needle and an opened proximal end,
- a power pack arranged inside the housing for expelling the medical product from the medical container, the power pack including a plunger rod configured to extend through the opened proximal end of the barrel for pushing a stopper arranged inside the barrel, the plunger rod being axially movable between an initial position and an injection end position distally located with respect to the initial position, and
- resilient adjustment means arranged between the plunger rod and the barrel for compensating clearances between the plunger rod and the barrel;
- wherein the resilient adjustment means are arranged on a plug attached to a distal end of the plunger rod; and
- wherein the plunger rod comprises a distal opening for receiving a connection portion of the plug and at least one axial slot configured to receive the resilient adjustment means.

2. The autoinjector according to claim 1, wherein the resilient adjustment means comprise a spring blade configured to deform in a radial inward direction so that the spring blade exerts a radial pushing force against the inner lateral wall of the barrel.

3. The autoinjector according to claim 1, wherein the spring blade has a fixed end secured to the plunger rod and a friction element configured to frictionally engage the inner lateral surface of the barrel.

4. The autoinjector according to claim 3, wherein the friction element is proximally located with regard to the fixed end.

5. The autoinjector according to claim 3, wherein the friction element is arranged at a free end of the spring blade.

6. The autoinjector according to claim 3, wherein the spring blade comprises an inclined outer side arranged between the fixed end and the friction element for easing insertion of the plunger inside the opened proximal end of the barrel.

7. The autoinjector according to claim 6, wherein the outer side has a convex and curved shape.

8. The autoinjector according to claim 1, wherein the resilient adjustment means are located at the distal end of the plunger rod.

9. The autoinjector according to claim 1, wherein the resilient adjustment means comprise a distal pushing area configured to push against the stopper.

10. The autoinjector according to claim 1, wherein the resilient adjustment means and the plug form a single piece.

11. The autoinjector according to claim 10, wherein the resilient adjustment means are overmolded on the plug.

12. The autoinjector according to claim 1, wherein the plug comprises a distal abutment surface configured to distally push against the stopper when the plunger rod moves to the injection end position.

13. The autoinjector according to claim 1, wherein the plug comprises a proximal shoulder configured to abut against a distal abutment surface of the plunger rod to stop insertion of the plug inside the plunger rod.

* * * * *